(12) United States Patent
Wietelmann et al.

(10) Patent No.: US 10,370,390 B2
(45) Date of Patent: Aug. 6, 2019

(54) METHOD FOR PRODUCING METAL ORGANYLS

(71) Applicant: ALBEMARLE GERMANY GMBH, Frankfurt am Main (DE)

(72) Inventors: Ulrich Wietelmann, Friedrichsdorf (DE); Christopher Kurth, Rodgau (DE); Stefan Scherer, Griesheim (DE); Peter Rittmeyer, Sulzbach/Taunus (DE); Armin Stoll, Hirschberg an der Bergstrase (DE)

( * ) Notice: Subject to any disclaimer, the term of this patent is extended or adjusted under 35 U.S.C. 154(b) by 0 days.

(21) Appl. No.: 15/563,240

(22) PCT Filed: Mar. 24, 2016

(86) PCT No.: PCT/EP2016/056533
§ 371 (c)(1),
(2) Date: Feb. 21, 2018

(87) PCT Pub. No.: WO2016/156193
PCT Pub. Date: Oct. 6, 2016

(65) Prior Publication Data
US 2018/0162880 A1    Jun. 14, 2018

(30) Foreign Application Priority Data

Apr. 2, 2015  (DE) .................. 10 2015 206 046
Apr. 16, 2015  (DE) .................. 10 2015 206 897

(51) Int. Cl.
| | |
|---|---|
| *C07F 1/00* | (2006.01) |
| *C07F 1/02* | (2006.01) |
| *C07F 1/04* | (2006.01) |
| *C07F 3/00* | (2006.01) |
| *C07F 3/02* | (2006.01) |
| *C07F 5/06* | (2006.01) |
| *C01B 6/04* | (2006.01) |

(52) U.S. Cl.
CPC .................. *C07F 1/02* (2013.01); *C01B 6/04* (2013.01); *C07F 1/00* (2013.01); *C07F 1/04* (2013.01); *C07F 3/00* (2013.01); *C07F 3/02* (2013.01); *C07F 5/066* (2013.01)

(58) Field of Classification Search
CPC ....... B01J 2231/323; C07F 5/066; C07F 1/02; C07F 3/02; C07F 3/00; C07F 1/04; C07F 1/00; C01B 6/04
See application file for complete search history.

(56) References Cited

U.S. PATENT DOCUMENTS

| | | |
|---|---|---|
| 3,706,809 A | 12/1972 | Tatsuo et al. |
| 3,998,941 A | 12/1976 | Nelson |
| 4,327,071 A | 4/1982 | Chiu et al. |
| 4,329,301 A * | 5/1982 | Bogdanovic ............... C07F 3/02 260/665 R |
| 4,554,153 A | 11/1985 | Bogdanovic |
| 4,792,620 A * | 12/1988 | Paulik .................. B01J 31/0231 560/232 |

FOREIGN PATENT DOCUMENTS

| | | |
|---|---|---|
| EP | 0003564 A1 | 8/1979 |
| EP | 0015541 A2 | 9/1980 |
| EP | 0014983 B1 | 12/1983 |
| EP | 0514707 | 11/1995 |
| EP | 0685425 A1 | 12/1995 |

OTHER PUBLICATIONS

Bartlett et al, Journal of the American Chemical Society, The Ethylenation of Secondary and Tertiary Alkyllithiums. II. Its Kinetics and the Nature of the Active Species, 1969, 91 (26), pp. 7425-7434. (Year: 1969).*
Kamienski, The University of Tennessee, Synthesis and Properties of Diorganomagnesium compounds, 1967, pp. 1-171. (Year: 1967).*
Norskov et al, Nature Chemistry, Towards the Computational Design of Solid Catalysts, 2009, 1, pp. 37-46. (Year: 2009).*
Grignard reaction, Wikipedia, Grignard reaction, recovered from https://en.wikipedia.org/wiki/Grignard_reaction on Jan. 28, 2019, pp. 1-8 (Year: 2019).*
Bogdanovic B et al; "Diorganomangnesium Compounds from Magnesium, Hydrogen, and 1-Alkenese and Their Application in Synthesis", European Journal of Inorganic Chemistry, Wiley-VCH Verlag, Weinheim, DD, vol. 126, No. 6, Jun. 1, 1993, pp. 1371-1383, XP002006062, ISSN: 1434-1948, DOI: 10.1002/CBER.19931260616.
International Search Report and Written Opinion of corresponding international application No. PCT/EP2016/056533 dated Nov. 18, 2016, all enclosed pages cited.
International Preliminary Report on Patentability of corresponding international application No. PCT/EP2016/056533 dated Oct. 3, 2017, all enclosed pages cited.
A. Maercker, Angew. Chem. Int. Ed. Engl. vol. 26, (1987) 972-989 (Corresponds to German version published as A. Maercker, Angew. Chem. vol. 99 (1987) 1002-1019).
C. G. Screttas, M. M. Screttas, J. Org. Chem. vol. 43, No. 6, (1978) 1064-1071.
B. Bogdanovic, B. Wermeckes, Angew. Chem. Int. Ed. Engl. vol. 20, No. 8 (1981) 684-685 (corresponds to German version published as: Bogdanovic, B. Wermeckes, Angew. Chem. vol. 93 (1981) 691).

(Continued)

*Primary Examiner* — Paul A Zucker

(74) *Attorney, Agent, or Firm* — Marcy M. Hoefling

(57) ABSTRACT

This invention provides a method for producing organometallic compounds $R_nM$ (M=alkali or alkaline earth element, R=alkyl residue) where n=valence of the metal M and R=alkyl residue with 2 to 18 C atoms. In the method of this invention, an olefin is hydrometalated in an alkyl methyl ether, or in a solvent mixture containing an alkyl methyl ether, by means of the metal M and in the presence of a hydrogen source and in the presence of a transition metal catalyst, wherein the molar ratio between alkyl methyl ether and metal M is at least 0.01:1 and at most 50:1.

5 Claims, No Drawings

(56) References Cited

OTHER PUBLICATIONS

E. C. Ashby, S. A. Noding, J. Org. Chem., vol. 45 (1980) 1041-1044.
A. Maercker, Angew. Chem. vol. 99 (1987) 1002-1019.
Becker et al, "Hydrogenolysis of the Grignard Reagent," J. Org. Chem., 1964, p. 954, vol. 29, Ethyl Corporation, Baton Rouge, LA.
Setijadi et al, "Remarkable hydrogen storage properties for nanocrystalline MgH2 synthesised by the hydrogenolysis of Grignard reagents," Phys. Chem. Chem. Phys., 2012, p. 11386-11397, vol. 14.
Lide, D.R., Handbook of Chemistry and Physics, 83rd Edition, 2002-2003.
Podall et al, Journal of Organic Chemistry, Reactions of Magnesium Hydride and Diethylmagnesium with Olefins, 1958, 23, pp. 1848-1852. (Year: 1958).
Liu et al, Journal of the American Chemical Society, Ti-Doped LiAl H4 for Hydrogen Storage: Synthesis, Catalyst Loading and Cycling Performance, 2011, 133, pp. 15593-15597. (Year 2011).

* cited by examiner

METHOD FOR PRODUCING METAL ORGANYLS

The subject matter of the present patent specification is a method for producing organometallic compounds $RM_n$ (M=alkali or an alkaline earth element, R=alkyl residue).

Alkali metal organyls have in part been known for more than 100 years, but only the readily soluble and thermally stable alkyl compounds of lithium RLi were able to gain broad preparative and industrially significant use. The first production of lithium organic compounds by W. Schlenk was carried out by cleaving mercury organic compounds by means of lithium metal (W. Schlenk, J. Holtz, Ber. Dtsch. Chem. Ges. 1917, 50, 262-274). This synthesis, starting with the toxic heavy metal mercury, obviously was not able to gain acceptance in industry. On the other hand, the convenient synthesis described for the first time by K. Ziegler and H. Colonius according to

  (1)

Hal=Cl, Br, I; R=alkyl or aryl forms the basis for the synthesis of lithium organic compounds (K. Ziegler, H. Colonius, Justus Liebigs Ann. Chem. 479 (1930) 135-149). The disadvantage of the Ziegler synthesis is that half of the expensive lithium metal produced by liquid melt electrolysis is consumed for the formation of the lithium halide byproduct. Instead of alkyl halides, functionalized organic compounds with leaving groups other than Hal⁻ can also be used, for example, ether (A. Maercker, Angew. Chem. Int. Ed. Engl. 26, (1987) 972) and thioether (C. G. Screttas, M. M. Screttas, J. Org. Chem. 43 (1978) 1064). In this case as well, only at most half of the lithium used is consumed:

  (2)

E=O or S

Similarly, in the catalytic lithiation of α-olefins according to B. Bogdanovic, in addition to the lithiated olefin compound (for example, vinyl lithium from ethene), a stoichiometric quantity of the unconsumed byproduct lithium hydride forms (B. Bogdanovic, B. Wermeckes, Angew. Chem. 94 (1981) 691; EP 0015541 A2).

The disadvantageous formation of a more or less useless or unconsumed byproduct such as LiHal, LiER' or LiH could be avoided in principle by direct hydrolithiation of olefins according to

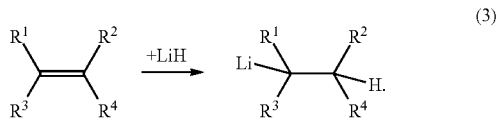  (3)

Unfortunately, commercial lithium hydride cannot be used for this purpose; instead, organolithium compounds containing a β-hydrogen atom in pure form or as solutions in hydrocarbons decompose according to the reversal of Eq. (3) (K. Ziegler, U. Gellert, Liebigs Ann. Chem. 1950, 567, 179):

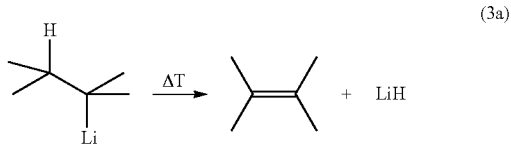  (3a)

E. C. Ashby et al. examined the suitability of active lithium hydride LiH*, produced by hydrogenolysis of t-butyllithium (t-BuLi) with hydrogen (approximately 100 bar), as reduction and hydrometalation agent (E. C. Ashby, S. A. Noding, J. Org. Chem. 1980, 45, 1041-1044). In the description of the invention, superscript asterisks ("*") are used to mark a highly reactive variant of the respective metal hydride. In the conversion of α-olefins with hyperstoichiometric quantities of LiH* into tetrahydrofuran (THF) and in the presence of also hyperstoichiometric quantities of $VCl_3$, certain olefins were converted quantitatively or nearly quantitatively into the saturated hydrocarbons. However, in the decomposition of the reaction mixture by means of $D_2O$, only a small amount of deuterium incorporation (29-30%) was observed. The authors assume that the reduction involves significant proportions of the corresponding organolithium species which react, by deuterolysis, to form the deuterated saturated hydrocarbons and thus can be trapped. In benzene as solvent, octene could be reduced in the presence of catalytic (5 mol %) transition metal concentrations and with the use of highly reactive LiH* to octane, or, after deuterolysis, to monodeutero octane. The best yields were achieved with the use of $Cp_2TiCl_2$ (77% octane, 50% D incorporation). This synthesis variant has the disadvantage that relatively large concentrations of transition metal catalyst (300% of the theory in the case of the reaction in THF) are necessary and that the organolithium compounds, which presumably formed in situ, decompose with H abstraction from the solvent (recognizable from the low D incorporation). In the reaction variant in benzene, the toxicity of the solvent and the again low RLi yield (deuterium incorporation maximum 50%) are disadvantageous. For these reasons, the organolithium synthesis via the hydrolithiation of olefins has never gained preparative relevance.

Alkyllithium compounds can be produced in anhydrous organic solvents, including ethers and hydrocarbons. With the exception of methyllithium, commercial products are marketed exclusively as solutions in hydrocarbons, because only such solutions are stable in storage. The strong lithium bases in fact attack functionalized solvents such as ethers already at room temperature and they decompose according to an α- or β-elimination mechanism with formation of lithium alcoholates and other byproducts. In the case of cyclic ethers such as tetrahydrofuran, for example, the ring opening with lithium enolate formation as a decomposition variant also occurs. Noncyclic ethers which have no β-H hydrogen as a rule can decompose only according to an α-H elimination mechanism, as has been demonstrated for dimethyl ether, for example (A. Maercker, Angew. Chem. 99 (1987) 1002-19). This decomposition mechanism occurs to a lesser degree for thermodynamic reasons. Nevertheless, it has been reported that the stability of lithium organyls, for example, of butyllithium, is poorer in pure dimethyl ether than in diethyl ether: the decomposition is approximately 10-20 times faster (K. Ziegler, H.-G. Gellert, Justus Liebigs Ann. Chem. 567 (1950) 185).

In a manner similar to alkali metal organyls, the dialkyl compounds of alkaline earth elements ($R_2M$) are also usually produced from elemental alkaline earth metal and alkyl halides:

  (4)

Hal=Cl, Br, I; M=Be, Mg, Ca, Sr, Ba

A direct synthesis of $R_2Mg$ compounds, for example, by hydrometalation of olefins analogously to Eq. (3) starting with commercial alkaline earth metal hydrides is not possible. Therefore, attempts have been made to produce the latter in a more reactive form. For example, highly reactive magnesium hydroxide can be obtained by high-pressure hydrogenation of Grignard compounds at higher temperatures (75-150° C., 350 bar) according to $$2RMgX+2H_2 \rightarrow 2RH+MgX_2+MgH_2* \quad (5)$$

(W. E. Becker, E. C. Ashby, J. Org. Chem. 29, 954 (1964)). Similarly, dialkylmagnesium compounds, for example, dibutylmagnesium, can also be converted by high-pressure hydrogenolysis (5 MPa) at 200° C. in MgH$_2$* (E. J. Setijadi, C. Boyer, Phys. Chem. Chem. Phys. 2012, 14, 11386-97). Due to the unfavorable conditions, the expensive Mg sources, and, in the case of the Grignard compounds, the unavoidable contamination with magnesium halides (MgX$_2$), this MgH$_2$* formation method has not gained any significance.

Moreover, a method for producing highly reactive magnesium hydride by hydrogenation of Mg metal in THF suspension and in the presence of a chromium-containing homogeneous catalyst has been described (B. Bogdanovic, P. Bons, S. Konstantinovic, M. Schwickardi, U. Westeppe, Chem. Ber. 1993, 126, 1371-83; U.S. Pat. No. 4,554, 153A1). The THF-soluble catalyst consists of a CrCl$_3$/Mg-anthracene complex; the hydrogenation runs only under high-pressure conditions (for example, 80 bar). According to EP 0014983 B1, the reactive magnesium hydride MgH$_2$* produced in this manner is reacted with an olefin in the presence of a transition metal catalyst selected from the group consisting of the halides of subgroups IV to VIII of the periodic table of elements (PTE) preferably in tetrahydrofuran in the temperature range of 0 to 200° C. and at a pressure from 1 to 300 bar. Dialkylmagnesium compounds with moderate to very good yields are obtained as solutions in THF. Due to the use of toxic chromium compounds and the necessary high hydrogen pressure in the MgH$_2$* production, this synthesis variant is also disadvantageous. Moreover, the fact that the solvent THF can be obtained by evaporation only very laboriously, incompletely and with acceptance of partial product decomposition, or by a crystallization method using large solvent quantities and with significant yield losses, is disadvantageous (experimental data in: B. Bogdanovic, P. Bons, S. Konstantinovic, M. Schwickardi, U. Westeppe, Chem. Ber. 1993, 126, 1371-83).

According to the method known from the document EP 514707 B1, magnesium hydride is activated before or during the reaction with an olefin by grinding to a particle size of ≤10 µm, preferably ≤1 µm without the addition of complex catalysts. In the reaction with olefin in an ether solvent, preferably THF or diglyme, a transition metal halide, as described in EP 0014983 B1 is added as catalyst. It is disadvantageous that as a rule the yields of dialkylmagnesium compounds are low (25-34%). Moreover, as before, the difficulty consists in obtaining ether-free (particularly THF-free) R$_2$Mg. Dialkylmagnesium compounds are used predominantly as magnesium source in the production of Ziegler Natta polyolefin catalysts. For various reasons, donor solvent-free (particularly THF-free) products are necessary for this application.

The aim of the invention is to indicate a method which, starting with inexpensive commercially available raw materials, enables, under mild conditions, the synthesis of organometallic compounds R$_n$M (M=alkali or alkaline earth metal, n=valence of the metal M, R=an alkyl group), wherein any active metal M (i.e., metal of oxidation state 0) can be converted into the desired organometallic compound R$_n$M without the formation of byproducts of little value, such as metal halides and the like, and it should be possible to isolate the organometallic compound without decomposition in a pure (solvent-free) form or as a solution in a non-donor solvent, particularly a THF-free non-donor solvent.

According to the invention, the aim is achieved in that olefins are converted by means of preformed MH$_n$" (Eq. 6) or by means of metal hydride formed in situ (Eq. 7) in an alkyl methyl ether (AME)-containing aprotic and anhydrous liquid phase. This is shown below using the example of the alkyllithium synthesis:

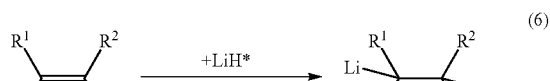
(6)

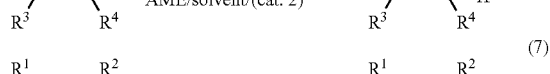
(7)

Surprisingly, it was found that, in an AME-containing solvent mixture, the hydrometalation with highly reactive metal hydride (Eq. 6 or similar with another alkali or alkaline earth metal) or under in situ conditions (Eq. 7 or analogously with other alkali or alkaline earth compounds) occurs directly and with good yields. In order to increase yields and reaction rates of the hydrometalation and also be able to use commercial, non highly reactive metal hydride, the presence of a transition catalyst ("cat. 2" in reaction equations (6) and (7)) is necessary. For the in situ formation of the highly reactive metal hydrides MH$_n$* according to reaction variant (7), the presence of highly reactive metal M$^2$* and/or of a compound having the general formula M$^1$$_x$[M$^2$(A$^1$$_y$A$^2$$_z$)$_{3+x}$]$_b$ (referred to as "cat. 1" in Eq. 7) is preferable for achieving a sufficiently high formation rate of the metal hydride MH$_n$*. The highly reactive M$^2$* must have a mean particle size D$_{50}$ between 0.01 and 100 µm and it must not be negatively affected, in terms of its reactivity, by previous contact with air, oxygen, moisture or other reactive substances. M$^2$* is preferably finely dispersed aluminum powder having the indicated mean particle size D50 between 0.01 and 100 µm. In the generic formula M$^1$$_x$[M$^2$(A$^1$$_y$A$^2$$_z$)$_{3+x}$]$_b$.

M$^1$=an alkali metal (Li, Na, K, Rb, Cs), an alkaline earth metal (Be, Mg, Ca, Sr, Ba) or an element from the group of the rare earths selected from Sc, Y, La, Ce, Pr, Nd, Pm, Eu, Gd, Tb, Dy, Ho, Er, Tm, Yb, Lu;

x=0 or 1;

M$^2$=an element of the 3rd main group of the PTE, selected from the B, Al, Ga or In;

A$^1$=H or an alkyl group, branched or unbranched, containing 1-18 C atoms, wherein the up to four A groups can be identical or different;

A$^2$=an alkoxy residue (OR with R=alkyl with 1-8 C atoms), a dialkylamino residue (NR$_2$ with R=alkyl with 1-8 C atoms) or a halogen selected Cl, Br, I;

y can assume the value 1, 2 or 3, wherein y+z=3;

b=the valence of M$^1$;

Suitable olefins contain 2 to 18 C atoms; olefins with terminal double bond are preferable, also referred to as α-olefins, i.e., olefins where R$^1$ and R$^3$=H. Particularly preferable are ethene, 1-propene, 1-butene, 1-pentene, 1-hexene, 1-heptene, 1-octene, 1-decene. Moreover, olefins with $R^2$ and $R^4$=alkyl groups containing 1-8 C atoms can be used, for example, 2-alkylprop-1-enes, 2-alkyl-1-butenes, 2-alkyl-1-hexenes (in each case with alkyl groups containing 1-8 C atoms). Under certain conditions, olefins with internal double bonds, for example, 2-butene, 2-pentene, 2-hexene, 2-heptene, 2-octene, 2-decene, can be accessed using the hydrolithiation reaction according to the invention.

For the hydrometalation according to Eq. 6, the commercially available metal hydrides, for example, commercial lithium hydride powder, cannot be used without the use of transition metal catalysts (cat. 2 in Eq. (6)), since they do not react.

Suitable donor solvents are ethers, particularly preferably alkyl methyl ethers R—O—$CH_3$ (AME) where R=alkyl residue, for example, dimethyl ether, methyl ethyl ether, methyl propyl ether, methyl butyl ether, methyl pentyl ether, methyl cyclopentyl ether, methyl hexyl ether. Dimethyl ether is most particularly preferable.

By the addition of a transition metal-containing catalyst (cat. 2 in Eq. 6 and 7), the rate of the hydrometalation can in part be clearly increased. As catalysts, one can consider using the halogen or alkoxy compounds of the 4th and 5th subgroup of the PTE, in particular the chlorides of Ti, Zr, Hf, V, Nb, Ta, as well as metallocene compounds of the mentioned metals, such as, for example, $Cp_2TiCl_2$, $CpTiCl_3$, $Cp_2ZrCl_2$, or other complex compounds of the mentioned metals. They are added in quantities from 0.001 to 10 mol %, preferably 0.005 to 5 mol % with respect to the metal hydride $MH_n$.

The metal hydride addition according to Eq. (6) or (7) (the reaction is represented for the example M=Li, these apply similarly for the other metal hydrides that can be used according to the invention) can occur in the temperature range between −40 and +150° C., preferably −20 and 100° C., particularly preferably 0 to 50° C. If, as AME, the particularly preferred dimethyl ether which is gaseous at room temperature (RT) is used, then the use of a pressurizing system and/or of a reflux cooler system (condenser) operated at low temperatures (for example, −40 to +20° C., depending on pressure) is indicated. Particularly preferable are mixtures of hydrocarbons and AMEs, most particularly preferably mixtures of saturated hydrocarbons such as pentane, hexane, heptane, octane, decane, dodecane or commercially available hydrocarbon mixtures such as technical hexane, technical heptane, or boiling fractions (petroleum ether) such as, for example, the petroleum ethers marketed under the trade name "Shellsole" by the company Shell, with dimethyl ether. The hydrocarbon content can constitute a proportion of up to 95% by weight, preferably up to 80% by weight, in the reaction mixture.

Since dimethyl ether dissolves satisfactorily in the mentioned hydrocarbons, a convenient, nearly pressureless process procedure is possible at particularly preferable reaction temperatures in the range between approximately 0 and 50° C. The AME content in the reaction mixture depends on the concentration of the metal M or of the metal hydride $MH_n$. The molar ratio between AME and M or $MH_n$ is at least 0.01:1 and at most 50:1, preferably at least 0.1:1 to 30:1 and particularly preferably 0.2:1 to 20:1.

In case a completely preformed reactive metal hydride is not used, and the metal hydride instead has to be generated first in situ according to Eq. 7, a catalyst "cat. 1," which is either a finely dispersed active metal $M^{2*}$ and/or compounds of general formula $M^1_x[M^2(A^1_yA^2_z)_{3+x}]_b$ should be added in stoichiometric quantities, or, in the presence of a source for hydrogen, in catalytic quantities. The molar ratio of catalyst to M or $MH_n$ is at least 0.0001:1 and at most 0.5:1, preferably at least 0.001:1 to 0.3:1, and particularly preferably 0.005:1 to 0.2:1. It was found surprisingly that the hydrogenation of M in the presence of highly reactive metal $M^{2*}$ and/or compounds of general generic formula $M^1_x[M^2(A^1_yA^2_z)_{3+x}]_b$ preferably under hydrogen atmosphere under mild conditions succeeds with high yield. The prerequisite is that the metal M has a more negative standard potential than the metal $M^2$ or $M^2$ in $M^1_x[M^2(A^1_yA^2_z)_{3+x}]_b$. Below, the respective standard potentials are summarized (D. R. Lide, Handbook of Chemistry and Physics 83$^{rd}$ ed., 2002-2003):

| 1st main group M= | Normal potential (V) | 2nd main group M= | Normal potential (V) | 3rd main group $M^2$= | Normal potential (V) |
|---|---|---|---|---|---|
| Li | −3.0401 | Be | −1.847 | B | |
| Na | −2.71 | Mg | −2.372 | Al | −1.662 |
| K | −2.931 | Ca | −2.868 | Ga | −0.539 |
| Rb | −2.98 | Sr | −2.899 | In | −0.3382 |
| Cs | −3.026 | Ba | −2.912 | | |

It is assumed that the hydrogen of $M^2$-H compounds is transferred to the base metals M and that the driving force of the reaction is in the formation of the thermodynamically more stable hydride(s). Due to the dehydrogenation of $M^1_{x[M^2}(A^1_yA^2_z)_{3+x}]_b$, elemental $M^{2*}$ forms; the latter is in an extremely reactive form (finely dispersed, in part amorphous form), and is very reactive with respect to hydrogen, for example, i.e., it is rehydrogenated in the presence of a hydrogen source. On this backdrop, it is understandable that the use of $M^1_{x[M^2}(A^1_yA^2_z)_{3+x}]_b$ or activated elemental $M^{2*}$ in catalytic quantities is sufficient.

As stoichiometric hydrogenation agent or hydrogenation catalyst, it is preferable to use compounds of aluminum $M^1_x[Al(A^1_yA^2_z)_{3+x}]_b$ or active/activated aluminum metal. In particular, the alkali alanates $LiAlH_4$ and $NaAlH_4$, $Na[H_2AlEt_2]$, which are produced on an industrial scale, are particularly suitable. Alane $AlH_3$ and alkylaluminum hydride such as diisobutylaluminum hydride can also be used with equal success.

Moreover, it was found surprisingly that certain non-hydride compounds of general formula $M^1_{x[M^2}(A^1_yA^2_z)_{3+x}]_b$ can also be used (thus such compounds in which neither $A^1$ nor $A^2$=H), when the hydrogen necessary for the hydrogenation of M is supplied in elemental form ($H_2$) or in molecularly stored form (for example, as 1,3-cyclohexadiene). Without being bound to the correctness of the hypothesis, it is assumed that, under hydrogenation conditions, a reactive form of the metal $M^{2*}$ or an alloy consisting of $M^2$ and M forms, which can take up hydrogen and transfer the hydrogen in a subsequent step to the base metal M. This is explained based on the example of the industrially available aluminum alkyls ($M^2$=Al). For example, if triethylaluminum is reacted with elemental lithium in AME-containing suspensions, then the formation of black, finely dispersed aluminum is observed, while the lithium dissolves at least partially:

$$4Et_3Al+3Li \rightarrow 3LiAlEt_4Ar\downarrow \qquad (8)$$

$$Et_3Al+3Li \rightarrow 3LiEt+Al\downarrow \qquad (8a)$$

$$LiEt+Et_3Al \rightarrow LiAlEt_4 \qquad (8b)$$

The finely dispersed Al* reacts readily with hydrogen to form $AlH_3$. The latter in turn can transfer the hydrogen under mild conditions to base metals M. In addition to triethylaluminum, trimethylaluminum and tributylaluminum can also be used, for example.

Similarly, by reacting $AlCl_3$ in AME-containing solutions by reaction with, for example, lithium metal, reactive elemental aluminum metal forms in addition to $LiAlCl_4$. The aluminates such as $Li[AlEt_4]$ can also react with hydrogen to form hydride-containing species.

In the in situ metal hydride synthesis according to Eq. 7, the reaction temperatures can be varied within broad ranges; as a rule they are between −20 and 150° C., preferably 0 and 100° C., and particularly preferably between 25 and 70° C. If a reaction procedure according to Eq. 7 or Eq. 8 is intended, contact with elemental hydrogen must be ensured. Frequently, a method of operation without overpressure is sufficient; but to achieve the shortest possible reaction times, it is possible to work under $H_2$ pressure conditions. Preferably, the $H_2$ overpressure is 2-300 bar, particularly preferably 10-100 bar. It is also possible to use, as hydrogen source, a compound which releases hydrogen under the selected work conditions. Examples are: 1,3-cyclohexadiene, decalin, N-ethylcarbazole.

It was found surprisingly that alkyl methyl ethers, particularly dimethyl ethers, can be separated simply and completely from the reaction product $MR_n$. This is surprising, since it is known to the person skilled in the art that, for example, dimethyl ether with a dipole moment of 1.3 debye (for comparison: diethyl ether=1.098 debye) is a strong Lewis base and a very strong donor solvent. It was found that it is often sufficient, according to the invention, to concentrate or evaporate the preferably clear filtered reaction mixture at room temperature or slightly elevated temperature (maximum 60° C.) preferably under vacuum conditions. If high boiling hydrocarbon cosolvents are used (they are preferably hydrocarbons with C chain lengths of at least 7, for example, heptane, octane, etc.), the low boiling dimethyl ether can be separated selectively by distillation. The alkyl metal compounds $MR_n$ are here obtained in the form of pure substances or solutions in hydrocarbons with AME residue contents of at most 20 mol %, preferably at most 5 mol % and particularly preferably at most 1 mol % with respect to $R_nM$ content and hydrocarbon contents up to at most 95% by weight.

Since the separation of the AMEs under industrially relevant conditions and at tolerable costs as a rule cannot be achieved entirely completely, products or product solutions according to the invention typically contain a residual content of AME and/or (depending on the storage duration and storage conditions) of non-volatile AME degradation products. The latter primarily consist of lithium methylate, which is formed by ether cleavage, as represented using the example M=Li and AME=dimethyl ether:

$$2R\text{—}Li + Me_2O \rightarrow R\text{—}(CH_2)\text{—}Li + MeO\text{—}Li + RH \qquad (9)$$

The products according to the invention contain at least 0.001 to at most 20 mol %, preferably 0.001 to at most 5 mol %, particularly preferably 0.001 to at most 1 mol % selected from AME (preferably dimethyl ether) and/or lithium methylate, with respect to metal organyl $R_nM$.

The invention claimed is:

1. A method for producing organometallic compounds $R_nM$ of the alkali or alkaline earth elements, where n=valence of the metal M and R=alkyl residue with 2 to 18 C atoms, characterized in that an α-olefin is hydrometalated in an aprotic and anhydrous liquid phase comprising an alkyl methyl ether wherein said alkyl methyl ether is selected from the group consisting of dimethyl ether, methyl ethyl ether, methyl propyl ether, methyl butyl ether, methyl pentyl ether, methyl cyclopentyl ether, and methyl hexyl ether,
   (a) by means of the metal M and in the presence of a hydrogen source for providing hydrogen, or
   (b) by means of active metal hydrides $MH_n$ in the presence of a halogen or alkoxy compound of the $4^{th}$ and $5^{th}$ sub group of the periodic table of elements as catalyst, wherein the metal M is selected from Li, Na, K, Rb, Cs, Ca, Sr, and Ba, and wherein the molar ratio between the alkyl methyl ether and the metal M is at least 0.01:1 and at most 50:1.

2. The method according to claim 1, characterized in that the α-olefin is selected from the group consisting of ethene, 1-propene, 1-butene, 1-pentene, 1-hexene, 1-heptene, 1-octene, 1-decene.

3. The method according to claim 1, characterized in that the alkyl methyl ether is dimethyl ether.

4. The method according to claim 1, characterized in that the molar ratio between the alkyl methyl ether and the metal M is at least 0.1:1 to 30:1.

5. The method according to claim 1, characterized in that the active metal hydrides $MH_n$ have a mean particle size $D_{50}$ of 0.01 to 100 μm.

* * * * *